(12) United States Patent
Onodera et al.

(10) Patent No.: US 10,830,909 B1
(45) Date of Patent: Nov. 10, 2020

(54) RADIOSCOPIC APPARATUS

(71) Applicant: SHIMADZU CORPORATION, Kyoto (JP)

(72) Inventors: Hiroki Onodera, Kyoto (JP); Masahiro Tanaka, Kyoto (JP); Keita Okutani, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 16/567,803

(22) Filed: Sep. 11, 2019

(30) Foreign Application Priority Data

May 28, 2019 (JP) .................................. 2019-099658

(51) Int. Cl.
*G01T 1/00* (2006.01)
*G01N 23/04* (2018.01)
(Continued)

(52) U.S. Cl.
CPC .......... *G01T 1/1635* (2013.01); *A61B 6/0407* (2013.01); *A61B 6/4014* (2013.01); *A61B 6/4452* (2013.01)

(58) Field of Classification Search
CPC ..... A61B 6/102; A61B 6/4266; A61B 6/4429; A61B 6/4441; A61B 6/547; A61B 6/037; A61B 6/0407; A61B 6/4258; A61B 6/4275; A61B 6/4291; A61B 6/4417; A61B 6/4494; A61B 6/5205; A61B 6/032; A61B 6/0487; A61B 6/08; A61B 6/4435; A61B 6/4452; A61B 6/4464; A61B 6/461; A61B 6/025; A61B 6/502; A61B 6/587; A61B 6/545; A61B 6/0414; A61B 6/06; A61B 6/40; A61B 6/42; A61B 6/4208; A61B 6/4283; A61B 6/44; A61B 6/4405; A61B 6/4411; A61B 6/4458; A61B 6/46; A61B 6/4007; A61B 6/4476; A61B 6/4482; A61B 6/487; A61B 6/50; A61B 6/588; A61B 6/5235; A61B 6/5247; A61B 6/5264; A61B 6/5276; A61B 6/584; A61B 6/585; G01T 1/1603; G21K 1/025; G06T 11/005; G06T 15/08; G06T 2207/10116; G06T 2207/30204; G06T 7/0012; G06T 5/50; G06T 7/73; G06T 11/006; G06T 2207/10121; G06T 2207/10124;
(Continued)

(56) References Cited

U.S. PATENT DOCUMENTS

2012/0014498 A1* 1/2012 Akahori ................. A61B 6/025
378/4
2016/0220218 A1* 8/2016 Zaiki ........................ A61B 6/54
(Continued)

FOREIGN PATENT DOCUMENTS

JP 11-188024 7/1999

*Primary Examiner* — Irakli Kiknadze
(74) *Attorney, Agent, or Firm* — Andrew F. Young, Esq.; Lackenbach Siegel, LLP

(57) ABSTRACT

A radioscopic apparatus includes a controller configured or programmed to, when imaging information using the first radiation source is selected, perform control of retracting a second detector to a position in one of longitudinal ends of a table, at which the second detector does not block radiation emitted from a first radiation source, according to information about a region to be imaged of a subject included in the selected imaging information.

9 Claims, 13 Drawing Sheets

(51) Int. Cl.
*G01T 1/163* (2006.01)
*A61B 6/00* (2006.01)
*A61B 6/04* (2006.01)

(58) Field of Classification Search
CPC ........... G06T 2207/20068; G06T 5/003; G06T 11/008; G06T 11/60; G06T 2207/20056; G06T 2207/20201; G06T 2207/20221; G06T 2207/30004; G06T 2207/30021; H04N 5/32
USPC .............................................. 378/1, 62, 208
See application file for complete search history.

(56) References Cited

U.S. PATENT DOCUMENTS

2017/0325773 A1* 11/2017 Nishino ................ A61B 6/5258
2018/0280727 A1* 10/2018 Takahashi ............ A61B 6/5205
2019/0060672 A1*  2/2019 Takahashi ............. A61B 6/548
2019/0374180 A1* 12/2019 Yoshida ............... A61B 6/4283

* cited by examiner

RADIOSCOPIC APPARATUS

CROSS-REFERENCE TO RELATED APPLICATIONS

This application claims the benefit of priority to Japanese Patent Application No. 2019-099658 filed on May 28, 2019. The entire contents of this application are hereby incorporated herein by reference.

BACKGROUND OF THE INVENTION

Field of the Invention

The present invention relates to a radioscopic apparatus.

Description of the Background Art

Conventionally, an X-ray diagnostic apparatus (radioscopic apparatus) including a first X-ray tube and a second X-ray tube is known. Such a radioscopic apparatus is disclosed in Japanese Patent Laid-Open No. 11-188024, for example.

In an X-ray diagnostic apparatus disclosed in Japanese Patent Laid-Open No. 11-188024, a first X-ray tube and a second X-ray tube are attached and held in such a manner as to face each other across a patient between opposite ends of a C-shaped arm. A first X-ray sensor and a second X-ray sensor are attached to and held by a screw rod (screw shaft) provided inside the C-shaped arm. When a user selects X-ray imaging with the first X-ray tube, the screw rod rotates such that the second X-ray sensor moves to a retracted position, and the first X-ray sensor moves to a position at which it can detect transmitted X-rays and stays thereat.

In Japanese Patent Laid-Open No. 11-188024, the first X-ray tube and the second X-ray tube are fixedly attached to the opposite ends of the C-shaped arm. Therefore, when the first X-ray tube is used, the second X-ray tube cannot be moved, and thus it is difficult to effectively use a space in which the second X-ray tube is disposed. Therefore, conventionally, in order to effectively use the space, an X-ray diagnostic apparatus (radioscopic apparatus) has been proposed in which a first X-ray sensor (first detector) and a second X-ray sensor (second detector) move independently of each other, and a first X-ray tube (first radiation source) and a second X-ray tube (second radiation source) move independently of each other.

However, in the aforementioned proposed conventional radioscopic apparatus, when the first radiation source is moved for imaging, it is necessary to retract the second detector to a position at which the second detector does not block radiation emitted from the first radiation source. In this case, when a user manually retracts the second detector, it takes time for the user to retract the second detector. In addition, when the radioscopic apparatus automatically retracts the second detector in a predetermined direction, the second detector may be retracted to the position at which the second detector blocks the radiation emitted from the first radiation source. In such a case, it is necessary for the user to manually move the second detector again.

SUMMARY OF THE INVENTION

The present invention has been proposed in order to solve the aforementioned problems, and an object of the present invention is to provide a radioscopic apparatus capable of reducing the work burden on a user by moving a second detector when using a first radiation source in the structure including a plurality of imagers each including a radiation source and a detector.

In order to attain the aforementioned object, a radioscopic apparatus according to as aspect of the present invention is configured to irradiate a subject with radiation and acquire a radiation image, and includes a table having a placement surface on which the subject is placed, a first imager including a first radiation source disposed on a side of the table opposite to the placement surface, and a first detector disposed at a position that faces the first radiation source with the table interposed therebetween, a second imager including a second detector disposed on the side of the table opposite to the placement surface and closer to the table than the first radiation source, and a second radiation source disposed opposite to the second detector with the table interposed therebetween, a storage configured to store imaging information including information about an imager to be used for imaging and information about a region to be imaged of the subject, and a controller configured or programmed to, when the imaging information using the first radiation source is selected, perform control of retracting the second detector to a position in one of longitudinal ends of the table, at which the second detector does not block the radiation emitted from the first radiation source, according to the information about the region to be imaged of the subject included in the selected imaging information.

The radioscopic apparatus according to this aspect of the present invention includes the storage configured to store the imaging information including the information about the imager to be used for imaging and the information about the region to be imaged of the subject, and the controller configured or programmed to, when the imaging information using the first radiation source is selected, perform control of retracting the second detector to the position in one of the longitudinal ends of the table, at which the second detector does not block the radiation emitted from the first radiation source, according to the information about the region to be imaged of the subject included in the selected imaging information. Accordingly, the imaging information includes the region to be imaged of the subject, and thus according to the information about the region to be imaged of the subject, the controller can acquire the position of the longitudinal end of the table suitable as the retracted position for the second detector. The region to be imaged refers to a portion of the subject on which fluoroscopy or imaging is to be performed using the first imager or the second imager.

Examples of the region to be imaged include internal organs such as a lung and a kidney, an oral cavity, a throat, and bones such as lumbar spines. Therefore, the second detector can be automatically retracted based on the acquired retracted position. Therefore, the second detector is automatically retracted to the position at which the second detector does not block the radiation emitted from the first radiation source such that it is not necessary for the user to manually retract the second detector, and thus the work burden on the user can be reduced.

In this case, the imaging information preferably further includes information about a retracted position for the second detector based on the region to be imaged, and the controller is preferably configured or programmed to perform control of retracting the second detector according to the information about the retracted position for the second detector when the imaging information using the first radiation source is selected. According to this structure, the imaging information includes the retracted position, and thus the controller can retract the second detector to the position at which the second detector does not block the radiation emitted from the first radiation source without acquiring, from the information about the region to be imaged, the position at which the second detector does not block the radiation emitted from the first radiation source.

In the radioscopic apparatus according to this aspect of the present invention, the controller is preferably configured or programmed to control the second detector to follow movement of the second radiation source and follow the second radiation source in a longitudinal direction of the table regardless of a position of the second radiation source in a short-side direction of the table. According to this structure, the controller controls the second detector to follow the movement of the second radiation source regardless of the position of the second radiation source in the short-side direction of the table such that the second detector can be caused to automatically follow the second radiation source without moving the second radiation source to a following start position. Consequently, the work burden on the user due to movement of the second detector can be further reduced.

In this case, the controller is preferably configured or programmed to control the second detector to follow the second radiation source by moving the second detector to a position of the second radiation source in the longitudinal direction of the table based on the position of the second radiation source in the longitudinal direction of the table when the imaging information using the second imager is selected and the second radiation source is manually moved. According to this structure, the second detector moves in the longitudinal direction of the table as the second radiation source is moved in the longitudinal direction of the table, and thus it is not necessary for the user to move the second detector in the longitudinal direction of the table. Consequently, the work burden on the user due to manual movement of the second detector can be reduced.

In this case, the controller is preferably configured or programmed to control the second detector to follow the second radiation source by moving the second detector to a first relative position based on the position of the second radiation source in the longitudinal direction of the table and an irradiation angle of the second radiation source with respect to the second detector. According to this structure, the first relative position can be acquired based on the position of the second radiation source in the longitudinal direction of the table and the irradiation angle of the second radiation source with respect to the second detector. Consequently, the controller can move the second detector to the first relative position based on the acquired information about the first relative position.

In this case, the imaging information preferably includes a plurality of imaging modes that specify imaging methods, and the controller is preferably configured or programmed to control the second detector to follow the second radiation source by moving the second detector to the first relative position or moving the second detector to a second relative position according to a selected imaging mode. According to this structure, the controller can move the second detector in the longitudinal direction of the table to the first relative position or the second relative position desired by the user. Consequently, it is not necessary for the user to adjust the position of the second detector in the longitudinal direction of the table according to the imaging mode, and thus the imaging mode can be quickly switched.

In the radioscopic apparatus in which the controller is configured or programmed to control the second detector to follow the second radiation source by moving the second detector to the first relative position or moving the second detector to the second relative position according to the selected imaging mode, the controller is preferably configured or programmed to control the second detector to follow the second radiation source by moving the second detector to the first relative position at which a central axis of the second radiation source and a longitudinal center of the second detector coincide with each other when the second detector is caused to follow the second radiation source. According to this structure, for example, in the case of an imaging mode in which the second radiation source is moved to capture a plurality of images of the same place from different angles, and a clear image is reconstructed from the plurality of captured radiation images, the center of the irradiation range of the second radiation source is aligned with the region to be imaged such that the longitudinal center of the second detector can coincide with the center of an imaging range.

In the radioscopic apparatus in which the controller is configured or programmed to control the second detector to follow the second radiation source by moving the second detector to the first relative position or moving the second detector to the second relative position according to the selected imaging mode, the controller is preferably configured or programmed to control the second detector to follow the second radiation source by moving the second detector to the second relative position at which an irradiation range of the second radiation source coincides with a longitudinal side of the second detector. According to this structure, the second detector can be aligned based on the irradiation range of the radiation emitted from the second radiation source, and thus the radiation that is not detected despite the fact that the radiation has been transmitted through the subject can be reduced. Consequently, exposure of the subject to extra radiation not related to acquisition of a radiation image can be significantly reduced or prevented.

In the radioscopic apparatus according to this aspect of the present invention, the second detector is preferably housed under the table or pulled out from under the table by manually moving the second detector in a short-side direction of the table, and the controller is preferably configured or programmed to perform control of moving a position of the second detector when the second detector is housed under the table. According to this structure, when the second detector is pulled out and only a portion of the subject is imaged, the second detector can be used as a table on which the region to be imaged is placed. In addition, the second detector moves in a state in which the second detector is housed, and thus collision of the second detector with the subject near the table can be significantly reduced or prevented.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

An embodiment of the present invention is hereinafter described with reference to the drawings.
(Structure of Radioscopic Apparatus)

The structure of a radioscopic apparatus 100 according to the embodiment is now described with reference to FIGS. 1 and 2.

Figure 1:
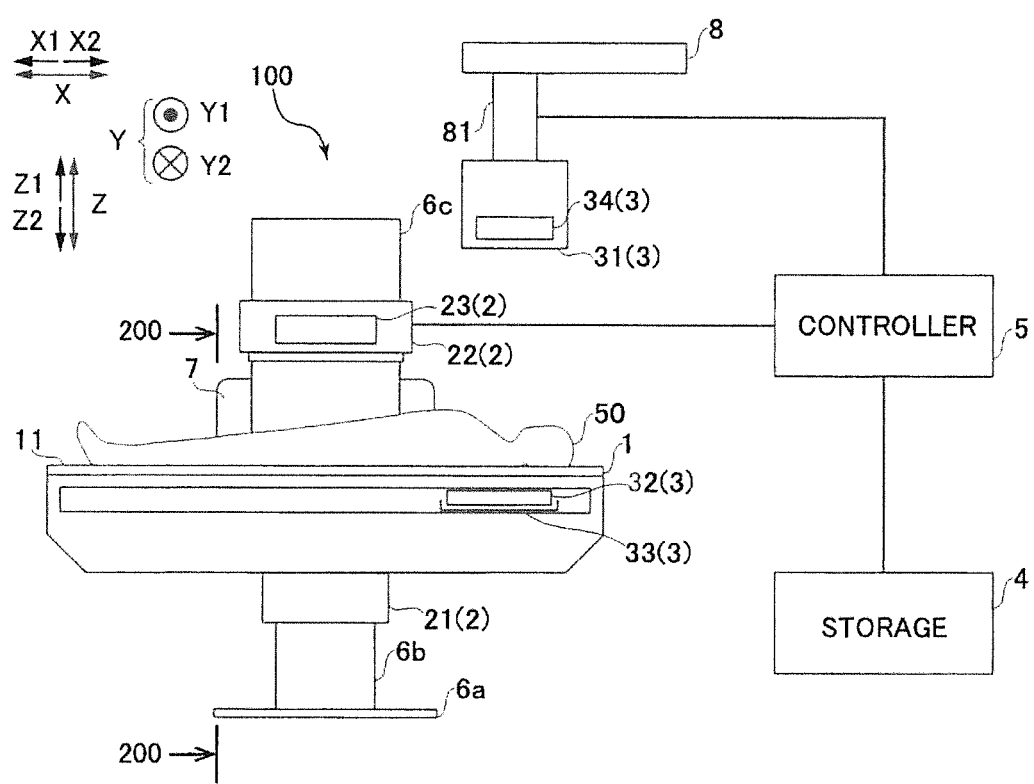
FIG. 1 is a schematic view showing the overall structure of a radioscopic apparatus.

As shown in FIG. 1, the radioscopic apparatus 100 includes a table 1, a first imager 2, a second imager 3, a storage 4, and a controller 5. The radioscopic apparatus 100 irradiates a subject 50 with X-rays to acquire an X-ray image. The X-rays are examples of "radiation" in the claims.

Figure 2:
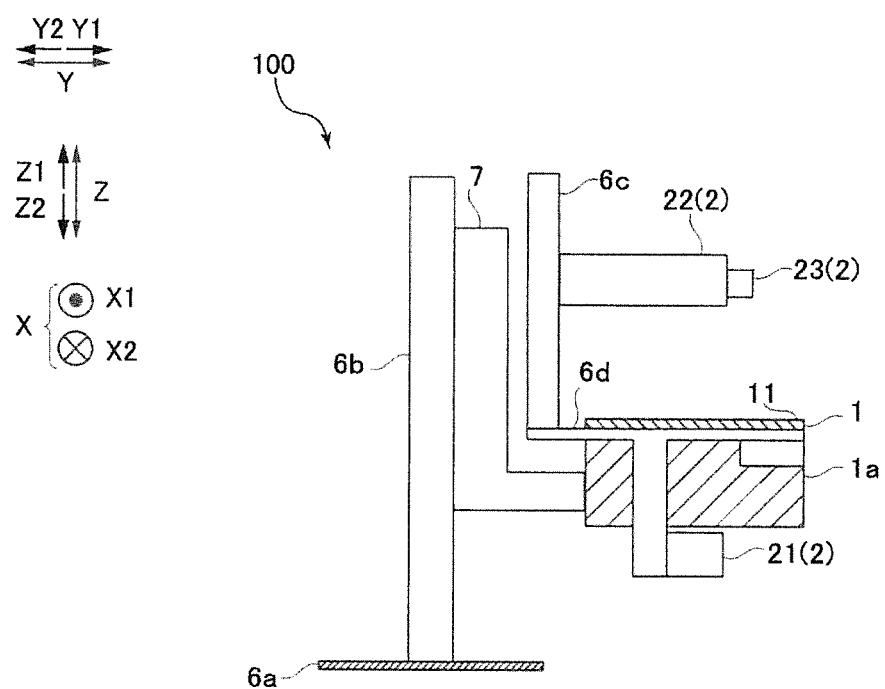
FIG. 2 is a sectional view taken along the 200-200 line in FIG. 1.

FIG. 2 is a sectional view taken along the line 200-200 of FIG. 1. Illustration of the subject 50 and the second imager 3 is omitted. As shown in FIG. 2, in the radioscopic apparatus 100, a first support 6b is fixed to a base 6a, and a main frame 1a on which the table 1 is mounted is held via a holder 7 by the first support 6b. Furthermore, a second support 6c is held via a connection member 6d by the main frame 1a, and the main frame 1a, the second support 6c, the holder 7, and the first support 6b are disposed in this order from the Y1 side toward the Y2 side. FIG. 2 shows an example of the structure of the radioscopic apparatus 100, and the shape of the connection member 6d is not particularly limited to this.

As shown in FIGS. 1 and 2, the table 1 has a placement surface 11 on which the subject 50 is placed. The subject 50 is placed along the longitudinal direction (X direction) of the placement surface 11 of the table 1. In the following description, the case in which the subject 50 is placed on the placement surface 11 in such a manner that the foot of the subject 50 is located on the X1 side and the head of the subject 50 is located on the X2 side is taken as an example.

The table 1 is moved up and down (in a Z direction) together with the second support 6c and the main frame 1a as the holder 7 is moved up and down in an upward-downward direction (Z direction) with the first support 6b as an axis by a drive (not shown). Furthermore, the table 1 is rotated together with the second support 6c and the main frame 1a as the holder 7 is rotated about the first support 6b by a rotation mechanism (not shown).

The first imager 2 is held by the second support 6c. The first imager 2 includes a first X-ray source 21 and a first detector 22. The first X-ray source 21 is disposed on the Z2 side of the second support 6c, and the first detector 22 is disposed on the Z1 side via the connection member 6d. The second imager 3 includes a second X-ray source 31 and a second detector 32. Each of the first X-ray source 21 and the second X-ray source 31 includes a tube that generates X-rays when a high voltage is applied thereto. The first X-ray source 21 is an example of a "first radiation source" in the claims, and the second X-ray source 31 is an example of a "second radiation source" in the claims.

The first X-ray source 21 is provided on the side (Z2 side) opposite to the placement surface 11 of the table 1. The first X-ray source 21 is held by the second support 6c. Therefore, as the second support 6c is moved in the longitudinal direction (X direction) of the table 1, the position of the first X-ray source 21 in the longitudinal direction (X direction) of the table 1 changes. In FIG. 1, the first X-ray source 21 emits X-rays toward the first detector 22 in a Z1 direction.

The first X-ray source 21 is used to perform fluoroscopy or imaging on a region 91 to be imaged of the subject 50 placed on the placement surface 11. The fluoroscopy refers to a method for acquiring an image of the region 91 to be imaged as a moving image while irradiating the region 91 to be imaged with X-rays. The imaging refers to a method for acquiring a still image of the region 91 to be imaged while irradiating the region 91 to be imaged with X-rays. The region 91 to be imaged includes internal organs such as a lung and a kidney, an oral cavity, a throat, and bones such as lumbar spines, for example. In the case of fluoroscopy, a user can perform treatment while causing the first X-ray source 21 to emit X-rays. The user who uses the first X-ray source 21 is a doctor, for example.

The first detector 22 is provided at a position (Z1 side) that faces the first X-ray source 21 with the placement surface 11 interposed therebetween. The first detector 22 is an image intensifier, for example. The first detector 22 detects X-rays emitted from the first X-ray source 21 and transmitted through the subject 50. The first detector 22 is held by the second support 6c via the connection member 6d. Therefore, as the second support 6c is moved in the longitudinal direction (X direction) of the table 1, the position of the first detector 22 in the longitudinal direction (X direction) of the table 1 changes. A handle 23 is attached to the first detector 22, and the user moves the second support 6c in the longitudinal direction (X direction) of the table 1 via the handle 23. A drive that drives the second support 6c includes a motor (not shown), and thus the user can easily move the first X-ray source 21 in the longitudinal direction (X direction) of the table 1.

The second detector 32 is disposed on the side (Z2 side) opposite to the placement surface 11 of the table 1. The second detector 32 is located between the first X-ray source 21 and the table 1 in the Z direction. The second detector 32 is a flat panel detector (FPD). The second detector 32 is disposed on a tray 33 that can be moved in the X direction under the table 1. The user can house the second detector 32 under the table 1 or pull out the second detector 32 from under the table 1 by moving the second detector 32 from the tray 33 in a Y direction. The Y direction refers to a direction orthogonal to the X direction and the Z direction, and refers to the short-side direction of the table 1 (see FIG. 6).

The second detector 32 detects X-rays emitted from the second X-ray source 31 and transmitted through the subject 50. The second detector 32 is used when the region 91 to be imaged of the subject 50 placed on the table 1 is imaged. In this case, the region 91 to be imaged includes internal organs such as a lung and a kidney, an oral cavity, a throat, and bones such as lumbar spines, for example. Furthermore, the user can pull out the second detector 32 from under the table 1 and place the region 91 to be imaged of the subject 50 on the second detector 32. The second detector 32 is also used when an X-ray image is acquired in a state in which the region 91 to be imaged of the subject 50 is placed thereon. In this case, the region 91 to be imaged is a hand, for example. The user can perform X-ray imaging of a bone of the hand while causing the second X-ray source 31 to emit X-rays. The user who uses the second X-ray source 31 is a radiographer, for example.

The second X-ray source 31 is attached to and suspended from a rail 8 disposed on the ceiling of a room in which the radioscopic apparatus 100 is disposed. The second X-ray source 31 emits X-rays toward the second detector 32.

The second X-ray source 31 is provided with a handle 34. The user can move the second X-ray source 31 in the X direction, the Y direction, and the Z direction via the handle 34. A drive 81 that moves the second X-ray source 31 includes a motor (not shown) that drives the second X-ray source 31. Therefore, the user can easily move the second X-ray source 31. Furthermore, the user can adjust the irradiation angle of the second X-ray source 31 with respect to the second detector 32 via the handle 34.

Figure 3:
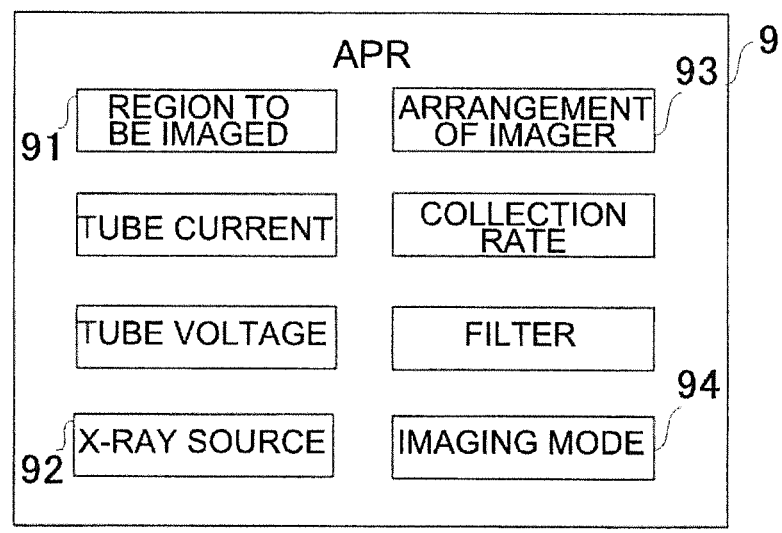
FIG. 3 is a diagram showing an example of an APR.

The storage 4 is a storage device of a personal computer, such as a read only memory (ROM) or a random access memory (RAM). The storage 4 stores an anatomic program (APR) 9. The APR 9 is an example of "imaging information" in the claims. The APR 9 is information stored for each region 91 to be imaged and used when imaging or fluoroscopy is performed. As shown in FIG. 3, the APR 9 is stored in which the region 91 to be imaged, an X-ray source 92 including information about the first X-ray source 21 or the second X-ray source 31 to be used, and the irradiation angle and dose of the first X-ray source 21 or the second X-ray source 31 to be used, the tube current of the first X-ray source 21 or the second X-ray source 31 to be used for imaging, and the tube voltage of the first X-ray source 21 or the second X-ray source 31 to be used for imaging are associated with each other.

In this embodiment, the APR 9 also includes information about the imager to be used for imaging among the first imager 2 and the second imager 3, an arrangement 93 of the imager including an arrangement of the first detector 22 and the second detector 23 at the time of imaging, a collection rate for the number of X-ray images to be captured, an imaging mode 94 for an X-ray image such as tomosynthesis, a filter used during X-ray irradiation, etc. The X-ray source 92 is an example of "information about an imager to be used for imaging" in the claims. The arrangement 93 of the imager is an example of "information about a retracted position for the second detector 32 based on the region to be imaged" in the claims.

As shown in FIG. 1, the controller 5 is a cabinet including a control board. Based on the APR 9 stored in the storage 4, the controller 5 controls the movement of the second detector 32 and controls the irradiation of the first X-ray source 21 and the second X-ray source 31. The number of control boards may be one, or plural according to a control target. The controller 5 performs control of retracting the second detector 32 when the APR 9 for imaging using the first imager 2 stored in the storage 4 is selected by the user.

When the APR 9 for imaging using the second imager 3 is selected by the user, the controller 5 controls the second detector 32 to follow the second X-ray source 31. In this case, the controller 5 performs control by switching between retraction and following of the second detector 32 according to the selected APR 9. The controller 5 acquires the position coordinates of the second X-ray source 31 and the second detector 32.

Imaging using the radioscopic apparatus 100 according to this embodiment is now described with reference to FIGS. 1 to 12.

(Imaging Using First Imager)

The case in which fluoroscopy or imaging using the first imager 2 is performed on the region 91 to be imaged is described. As shown in FIGS. 1 and 3, the user selects, from the storage 4, the APR 9 relating to the region 91 to be imaged on which fluoroscopy or imaging is to be performed. Selection of the APR 9 is performed by operating an operation unit (not shown) provided on the radioscopic apparatus 100. Then, the user moves the first X-ray source 21 to the region 91 to be imaged of the subject 50 via the handle 23.

Figure 4:
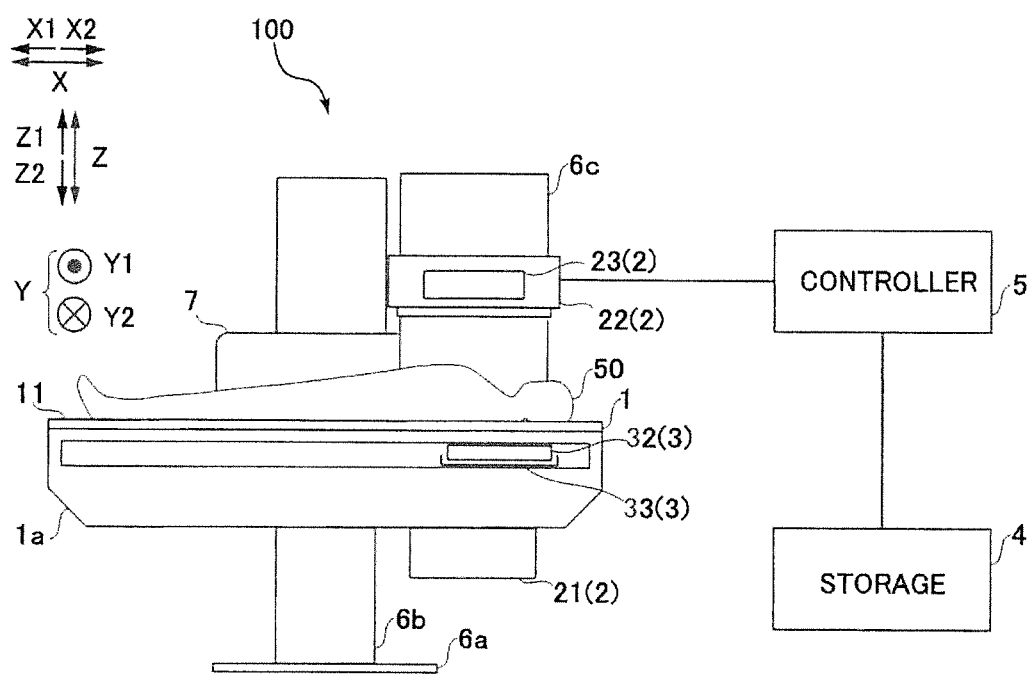
FIG. 4 is a diagram showing an example of an arrangement of a first imager and a second detector.

For example, as shown in FIG. 4, when selecting the APR 9 in which the chest (lung) of the subject 50 is the region 91 to be imaged, the user places the first X-ray source 21 and the first detector 22 at the chest. In FIG. 4, illustration of the second X-ray source 31 is omitted.

Figure 5:
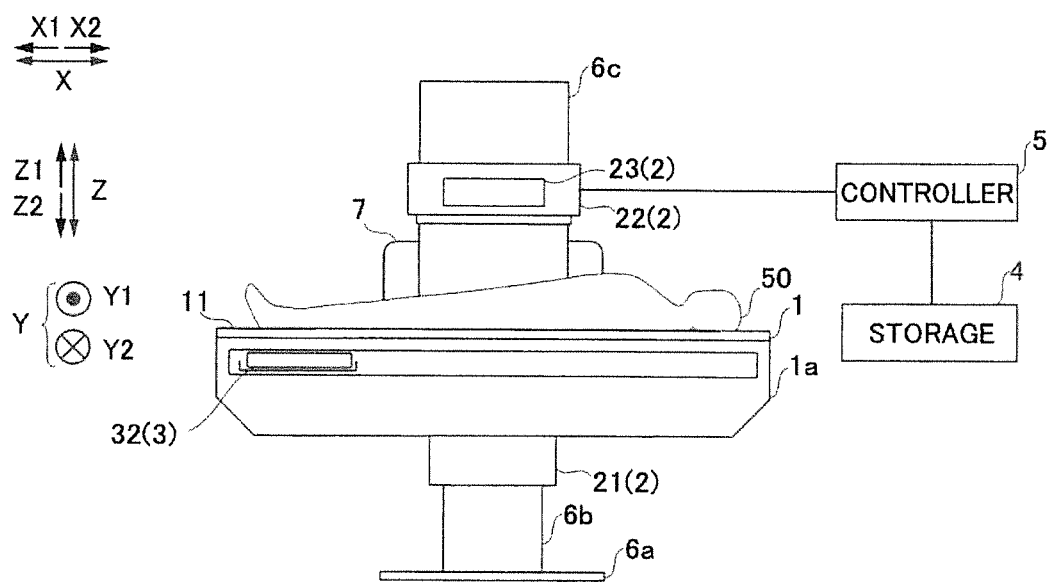
FIG. 5 is a diagram showing an example of a retracted position for the second detector.

As shown in FIG. 5, the controller 5 performs control of retracting the second detector 32 based on the information included in the selected APR 9. The controller 5 acquires the retracted position from information about the region 91 to be imaged, for example. The controller 5 performs control of retracting the second detector 32 according to the information about the region 91 to be imaged when the APR 9 includes the information about the region 91 to be imaged. When information about the retracted position for the second detector 32 is stored in the APR 9, the controller 5 performs control of retracting the second detector 32 according to the information about the retracted position. In FIG. 5, illustration of the second X-ray source 31 is omitted.

The controller 5 performs control of retracting the second detector 32 in a state in which the second detector 32 is housed in the tray 33 disposed under the table 1. When the second detector 32 is housed in the tray 33, the second detector 32 contacts a switch (not shown) provided in the tray 33. The controller 5 performs control of retracting the second detector 32 as the second detector 32 contacts the switch. The radioscopic apparatus 100 starts imaging after the second detector 32 is retracted.

(When Region to be Imaged is Stored in APR)

The controller 5 acquires the retracted position for the second detector 32 based on the region 91 to be imaged stored in the APR 9. The region 91 to be imaged is stored in the APR 9, and thus the controller 5 can distinguish whether the region 91 to be imaged is on the head side or the foot side. Therefore, the controller 5 acquires, as the retracted position, the foot side when the region 91 to be imaged is on the head side and the head side when the region 91 to be imaged is on the foot side. When the APR 9 stores imaging using the first X-ray source 21 and a chest as the region 91 to be imaged, the controller 5 calculates an end of the table 1 on the X1 side, and performs control of moving the second detector 32 to the calculated end.

(When Retracted Position is Stored in APR)

When the retracted position for the second detector 32 is further stored in the APR 9 stored in the storage 4, the controller 5 performs control of retracting the second detector 32 to one of longitudinal (X direction) ends of the table 1 according to the selected imaging condition. The user sets, as the retracted position, the foot side when the region 91 to be imaged is on the head side and the head side when the region 91 to be imaged is on the foot side. In the case of FIG.

4, the region 91 to be imaged is a chest, and thus the user stores, in the storage 4, information that the second detector 32 is to be retracted to the foot side (X1 side).

(Imaging Using Second Imager)

Imaging using the second imager 3 includes the case in which the subject 50 is placed on the table 1 for imaging, and the case in which the second detector 32 is pulled out from under the table 1 and the region 91 to be imaged of the subject 50 is placed on the second detector 32 for imaging. Imaging using the second imager 3 also includes the case in which the second X-ray source 31 emits X-rays from directly above the second detector 32 (in the Z direction), and the case in which the second X-ray source 31 emits X-rays while being inclined with respect to the second detector 32. Imaging using the second imager 3 in the case in which the second X-ray source 31 emits X-rays from directly above the second detector 32 is hereinafter described.

(Imaging in Case in which Subject is Placed on Table)

As shown in FIGS. 1 and 3, the user selects, from the storage 4, the APR 9 relating to the region 91 to be imaged on which fluoroscopy or imaging is to be performed. Selection of the APR 9 is performed by operating the operation unit (not shown) provided on the radioscopic apparatus 100. Then, the user moves the second X-ray source 31 to the region 91 to be imaged of the subject 50. In this case, the controller 5 controls the second detector 32 to follow the second X-ray source 31 moved by the user. Specifically, the controller 5 calculates the position coordinates of the second X-ray source 31 based on the amount of movement of the second X-ray source 31 detected by a position detector (not shown) such as a potentiometer. Then, the controller 5 causes the second detector 32 to follow the second X-ray source 31 by moving the second detector 32 in the longitudinal direction (X direction) of the table 1.

(Imaging in Case in which Region to be Imaged of Subject is Placed on Second Detector)

The case in which the second detector 32 is pulled out from under the table 1 and the region 91 to be imaged of the subject 50 is placed on the second detector 32 for imaging is now described. As shown in FIGS. 1 and 3, the user selects, from the storage 4, the APR 9 relating to the region 91 to be imaged on which fluoroscopy or imaging is to be performed. Selection of the APR 9 is performed by operating the operation unit (not shown) provided on the radioscopic apparatus 100.

Figure 6:
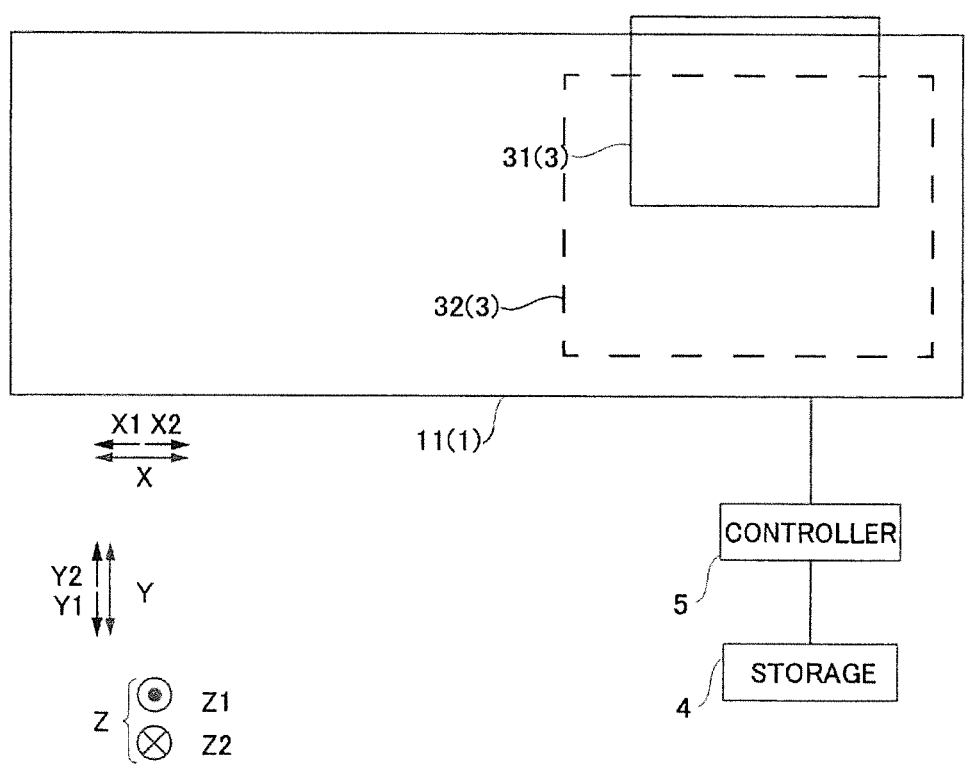
FIG. 6 is a diagram showing an example of the positional relationship between a table, a second X-ray source, and the second detector.
Figure 7:
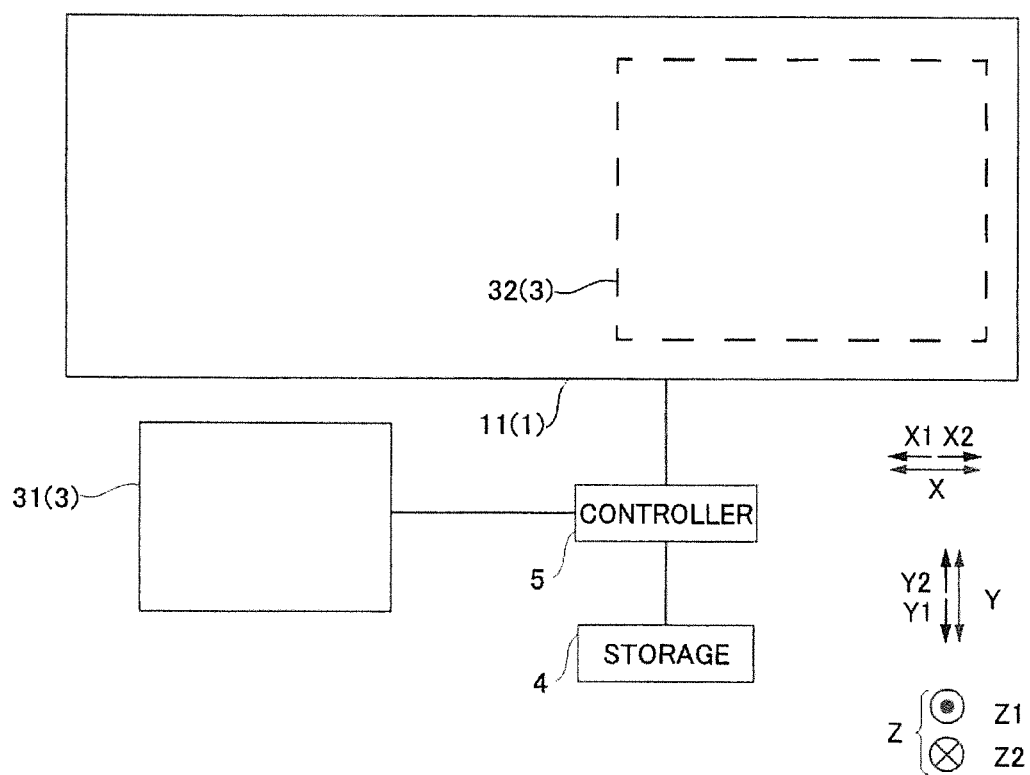
FIG. 7 is a diagram showing movement of the second X-ray source.

FIGS. 6 to 9 are diagrams of the table 1 as viewed from the Z1 direction side. As shown in FIG. 6, the second detector 32 is housed in the tray 33 disposed under the table 1. The second detector 32 is indicated by a dotted line because it is housed under the table 1 and cannot be seen from the Z1 direction side. In FIGS. 6 to 9, illustration of the first X-ray source 21 and the first detector 22 is omitted. As shown in FIG. 7, the user moves the second X-ray source 31 to a position to which the second detector 32 is pulled out for imaging. The controller 5 controls the second detector 32 to follow the second X-ray source 31 moved by the user.

Figure 8:
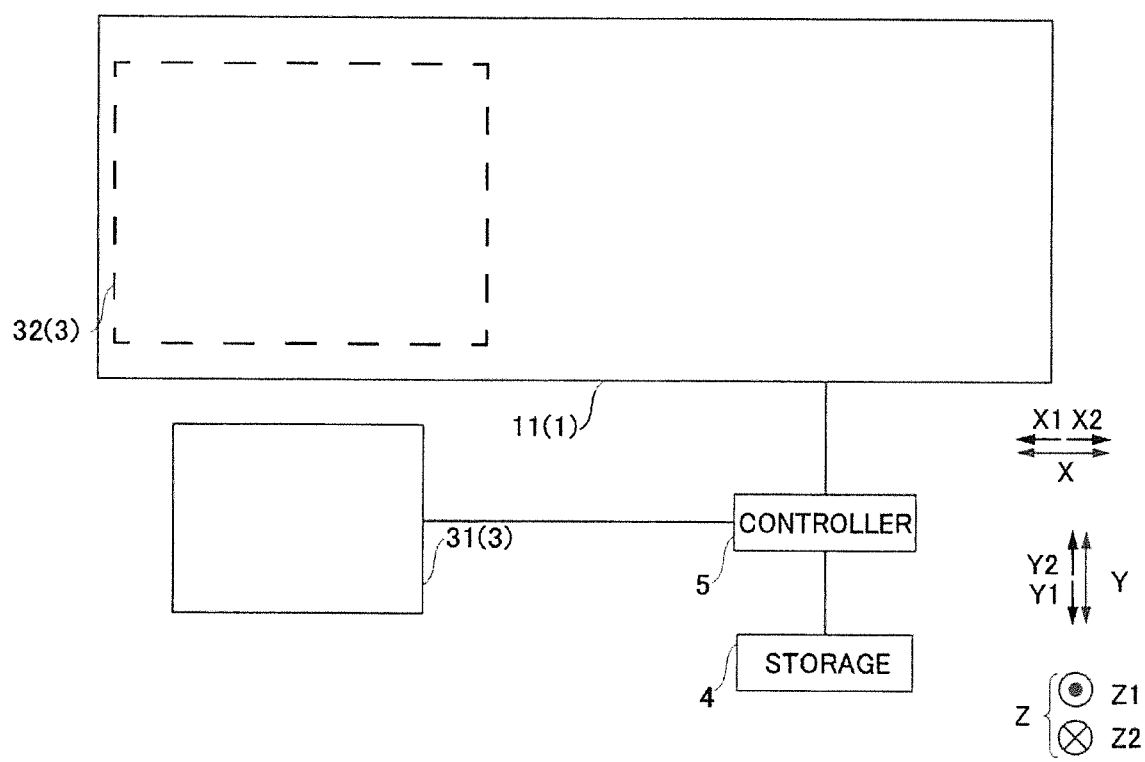
FIG. 8 is a diagram showing a state in which the second detector has moved and followed the second X-ray source along with the movement of the second X-ray source.

Specifically, the controller 5 calculates the position coordinates of the second X-ray source 31 based on the amount of movement of the second X-ray source 31 detected by the position detector (not shown) such as a potentiometer. Then, as shown in FIG. 8, the controller 5 causes the second detector 32 to follow the second X-ray source 31 by moving the second detector 32 in the longitudinal direction (X direction) of the table 1. In a state in which the second detector 32 is housed below the table 1, the controller 5 controls the second detector 32 to follow the second X-ray source 31.

Figure 9:
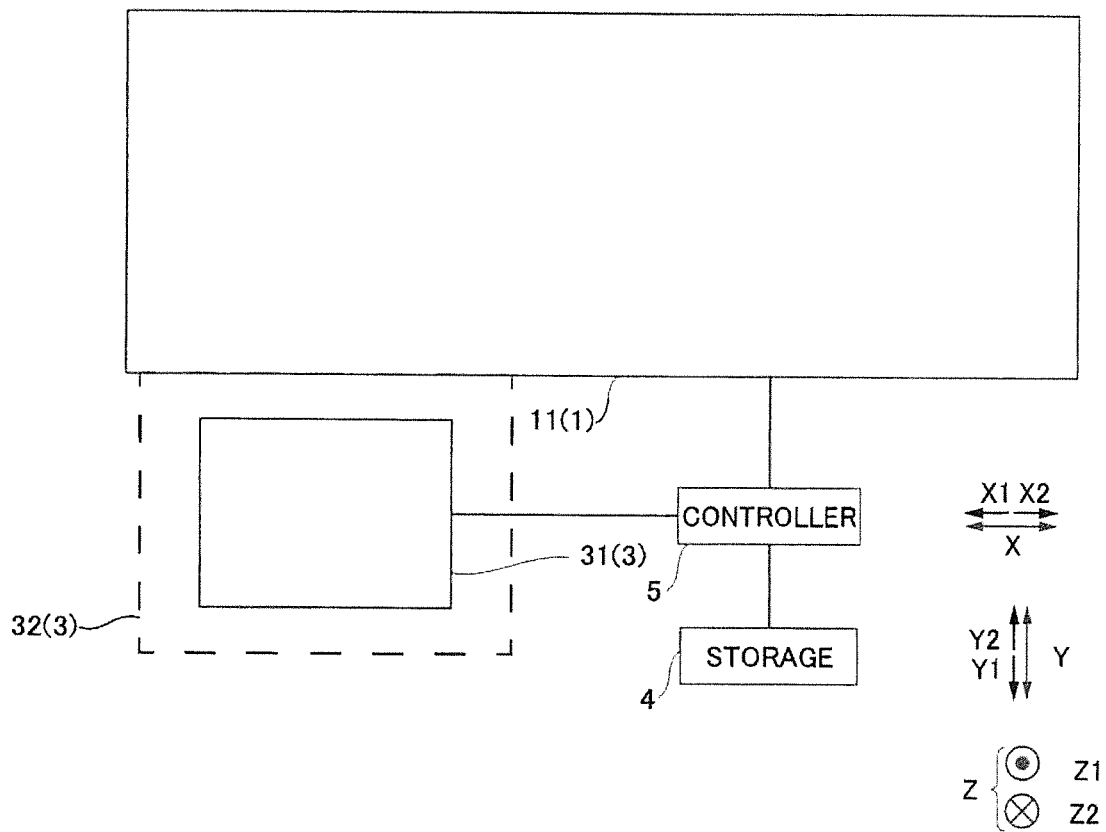
FIG. 9 is a diagram showing a state in which the second detector has been pulled out.

As shown in FIG. 9, the user pulls out the second detector 32 in a Y1 direction and places the second detector 32. The second detector 32 is fixed to the radioscopic apparatus 100 in the pulled-out state.

Next, imaging using the second imager 3 in the case in which the second X-ray source 31 irradiates X-rays while being inclined for imaging is described. In the following description, the case in which the second detector 32 is pulled out from under the table 1 and the region 91 to be imaged of the subject 50 is placed on the second detector 32 for imaging is described as an example.

When the second detector 32 is pulled out from below the table 1 and the region 91 to be imaged of the subject 50 is placed on the second detector 32 for imaging, there are various imaging modes. For example, the various imaging modes include a mode in which one image or a plurality of images of the same place are captured without changing the angle and a mode in which a plurality of images of the same place are captured while changing the angle. The controller 5 controls the second detector 32 to follow the second X-ray source 31 by moving the second detector 32 to a first relative position or by moving the second detector 32 to a second relative position according to the selected mode.

(First Relative Position)

Figure 10:
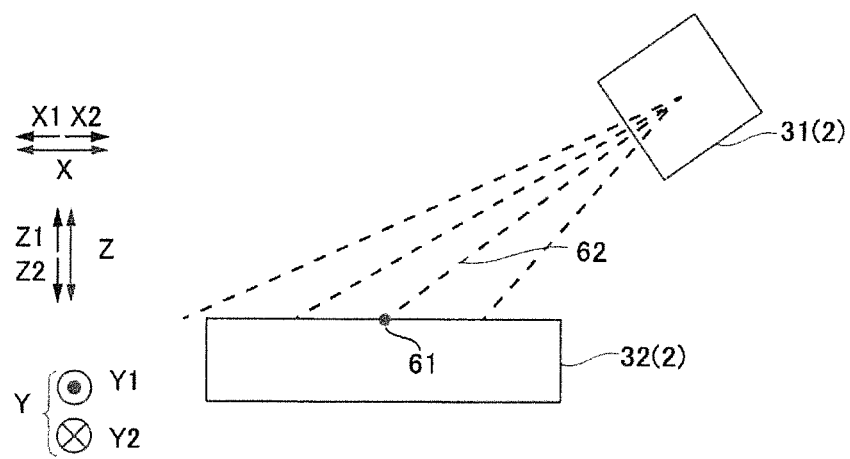
FIG. 10 is a diagram showing an example of a first relative position.

As shown in FIGS. 1 and 10, when the imaging condition using the second X-ray source 31 is selected and the second X-ray source 31 is moved by the user, the controller 5 moves the second detector 32 to the first relative position at which the longitudinal center 61 of the second detector 32 and the central axis 62 (X-ray optical axis) of the second X-ray source 31 coincide with each other. The controller 5 controls the second detector 32 to follow the second X-ray source 31 such that the second detector 32 continues to be located at the first relative position even when the second X-ray source 31 is moved. In FIG. 10, X-rays are indicated by dotted lines.

(Second Relative Position)

Figure 11:
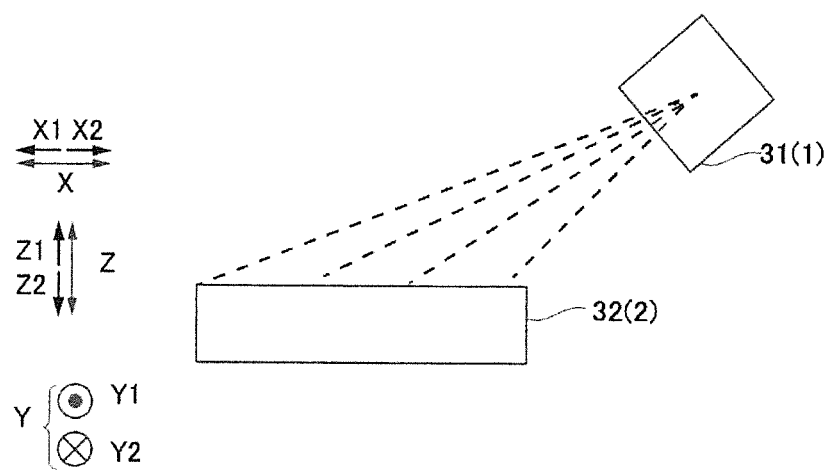
FIG. 11 is a diagram showing an example of a second relative position.
Figure 12:
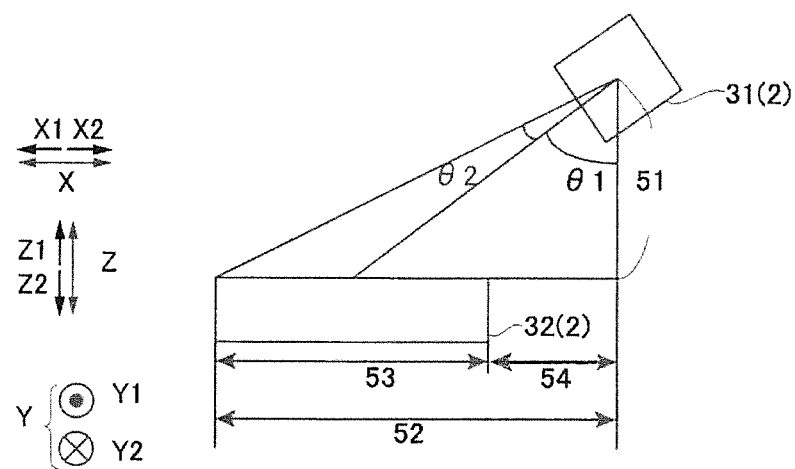
FIG. 12 is a diagram showing an example of the positional relationship between the second X-ray source and the second detector.

As shown in FIG. 11, the second relative position refers to a position at which the second detector 32 and the irradiation range of the second X-ray source 31 coincide with each other. The controller 5 performs control of adjusting the irradiation range of the second X-ray source 31 according to the imaging mode selected from the APR by the user. As shown in FIG. 12, the irradiation range of the second X-ray source 31 is narrowed in such a manner that based on a source to image distance (SID) 51, which is a distance between the second X-ray source 31 and the second detector 32, a field of view (FOV) 52, which is the irradiation field of the second X-ray source 31, and the irradiation angle θ1 of the central axis 62 of the second X-ray source 31, a difference 54 between the FOV 52 of the second X-ray source 31 and the length 53 of the second detector 32 in the longitudinal direction becomes zero. Specifically, the opening amount of a collimator in which the irradiation range of the second X-ray source 31 matches the length 53 of the second detector 32 in the longitudinal direction is calculated using the following equation (1). The opening amount of the collimator can be obtained by calculating an angle θ2 when the collimator is opened in an X1 direction or an X2 direction from the optical axis by θ2. The controller 5 performs control of narrowing the irradiation range of the second X-ray source 31 based on the calculation result. In FIG. 11, X-rays are indicated by dotted lines.

$$FOV = SID \times \tan(\theta_1 + \theta_2) - SID \times \tan(\theta_1 - \theta_2) \quad (1)$$

The controller 5 adjusts the opening amount of the collimator from the angle θ2 calculated by the equation (1). Thus, the longitudinal side of the second detector 32 coincides with the irradiation range of the second X-ray source 31.

The radioscopic apparatus 100 is configured to be able to select the imaging mode and the control to be performed by the controller 5. The imaging mode includes a mode in which an X-ray image of the region 91 to be imaged is captured without changing the irradiation angle of the second X-ray source 31 and a mode in which an X-ray image of the region 91 to be imaged is continuously captured while changing the irradiation angle of the second X-ray source 31, and a high-sensitivity X-ray image is acquired from a plurality of captured X-ray images. The control to be performed by the controller 5 includes controlling the second detector 32 to follow the second X-ray source 31 by moving the second detector 32 such that the central axis 62 of the second X-ray source 31 coincides with the longitudinal center of the second detector 32 and controlling the second detector 32 to follow the second X-ray source 31 by moving the second detector 32 such that the longitudinal side of the second detector 32 coincides with the irradiation range of the second X-ray source 31.

(Operation of Radioscopic Apparatus)

Figure 13:
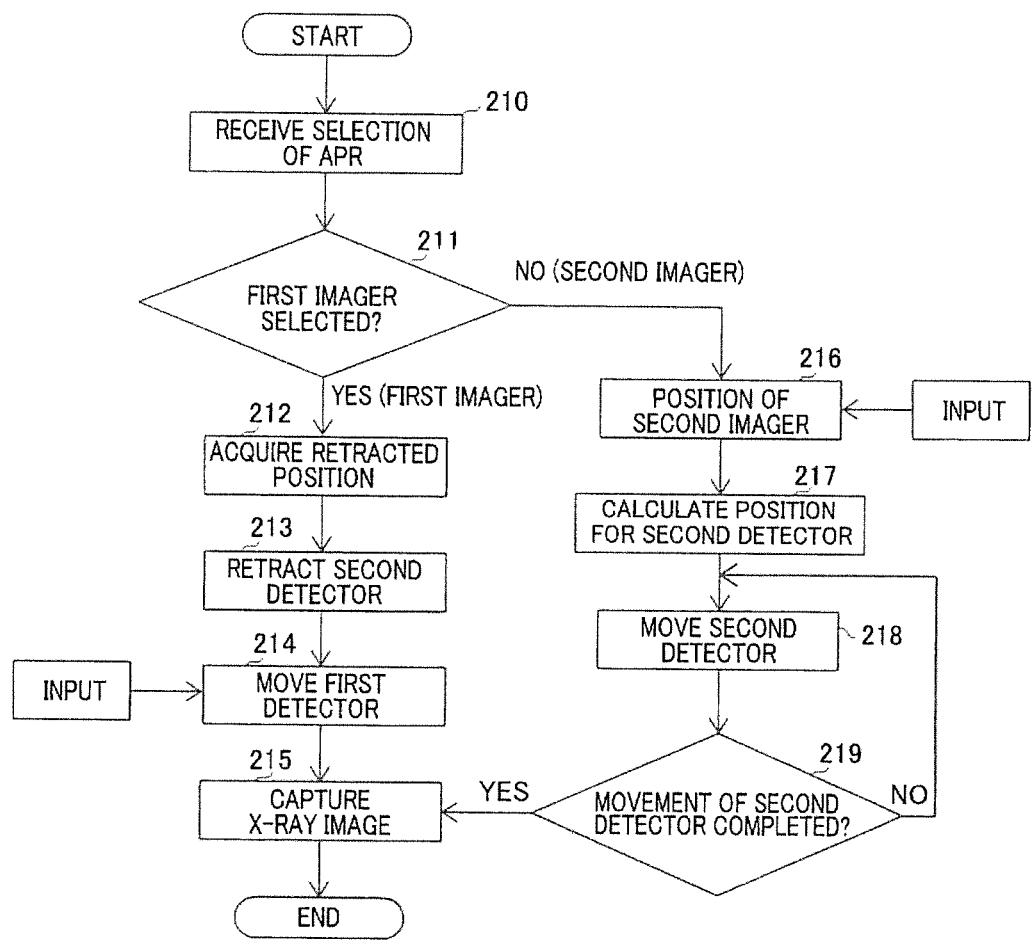
FIG. 13 is a diagram showing the processing operation of the radioscopic apparatus.

The operation of the radioscopic apparatus 100 is now described with reference to FIG. 13.

In step 210, the controller 5 receives selection of one APR 9 from a plurality of APRs 9 stored in the storage 4.

In step 211, the controller 5 changes control to be performed next depending on whether the imager to be used for imaging stored in the selected APR 9 is the first imager 2 or the second imager 3. In the case of imaging using the first imager 2, the controller 5 performs control in step 212. In the case of imaging using the second imager 3, the controller 5 performs control in step 216.

In step 212, the controller 5 acquires the retracted position for the second detector 32 from the selected APR 9. When the selected APR 9 includes the information about the retracted position for the second detector 32, the retracted position for the second detector 32 is acquired from the information about the retracted position. When the selected APR 9 does not include the information about the retracted position for the second detector 32, the retracted position for the second detector 32 is acquired based on the information included in the APR 9. For example, the retracted position for the second detector 32 is acquired based on the information about the region 91 to be imaged.

In step 213, the controller 5 performs control of retracting the second detector 32 to the retracted position for the second detector 32 acquired in step 212.

In step 214, the second support 6c is moved via the handle 23 by the user. As the second support 6c is moved, the first detector 22 and the first X-ray source 21 move. In FIG. 13, the movement by the user is described as "input".

In step 215, the controller 5 controls the first X-ray source 21 to irradiate a target region with X-rays. Then, capturing of an X-ray image starts.

When the imager to be used for imaging stored in the selected APR 9 is the second imager 3, the processing advances from step 211 to step 216.

In step 216, the controller 5 acquires the position coordinates of the second X-ray source 31 that has been moved to the region 91 to be imaged in advance by the user. In FIG. 13, the movement by the user is described as "input".

In step 217, the controller 5 acquires a position to which the second detector 32 is to be moved based on the position coordinates of the second X-ray source 31 acquired in step 216. At this time, the first relative position or the second relative position is acquired according to the mode stored in the selected APR 9.

In step 218, the controller 5 moves the second detector 32 to the position to which the second detector 32 is to be moved, which has been acquired in step 217. In step 218, the second detector 32 is moved only when the second detector 32 is housed below the table 1. When the second detector 32 is pulled out from under the table 1 and used, the user pulls out the second detector 32 from under the table 1 after the second detector 32 is moved.

In step 219, the controller 5 changes control depending on whether or not the movement of the second detector 32 is completed. In step 219, when the movement of the second detector 32 is completed, the controller 5 advances to step 215 and starts X-ray imaging. When the movement of the second detector 32 is not completed, the controller 5 returns to step 218 and moves the second detector 32.

Advantages of This Embodiment

According to this embodiment, the following advantages are obtained.

According to this embodiment, as described above, the radioscopic apparatus 100 includes the storage 4 configured to store the imaging information including the information about the imager to be used for imaging and the information about the region 91 to be imaged of the subject 50, and the controller 5 configured or programmed to, when the imaging information using the first X-ray source 21 is selected, perform control of retracting the second detector 32 according to the information about the region 91 to be imaged of the subject 50 included in the selected imaging information. Accordingly, the imaging information includes the region 91 to be imaged of the subject 50, and thus according to the information about the region 91 to be imaged of the subject 50, the controller 5 can acquire the position of the longitudinal end of the table 1 suitable as the retracted position for the second detector 32. Therefore, the second detector 32 can be automatically retracted based on the acquired retracted position. Therefore, the second detector 32 is automatically retracted to a position at which the second detector 32 does not block the X-rays emitted from the first X-ray source 21 such that it is not necessary for the user to manually retract the second detector 32, and thus the work burden on the user can be reduced.

According to this embodiment, the imaging information includes the information about the retracted position for the second detector 32 based on the region 91 to be imaged, and the controller 5 is configured or programmed to perform control of retracting the second detector 32 according to the information about the retracted position for the second detector 32 when the imaging information using the first X-ray source 21 is selected. Accordingly, the imaging information includes the retracted position, and thus the controller 5 can retract the second detector 32 to the position at which the second detector 32 does not block the X-rays emitted from the first X-ray source 21 without acquiring, from the information about the region 91 to be imaged, the position at which the second detector 32 does not block the X-rays emitted from the first X-ray source 21.

According to this embodiment, the controller 5 is configured or programmed to control the second detector 32 to follow movement of the second X-ray source 31 and follow the second X-ray source 31 in the longitudinal direction of the table 1 regardless of the position of the second X-ray source 31 in the short-side direction of the table 1. Accordingly, the controller 5 controls the second detector 32 to follow the movement of the second X-ray source 31 regardless of the position of the second X-ray source 31 in the short-side direction of the table 1 such that the second detector 32 can be caused to automatically follow the second X-ray source 31 without moving the second X-ray source 31 to a following start position. Consequently, the work burden on the user due to movement of the second detector 32 can be further reduced.

According to this embodiment, the controller 5 is configured or programmed to control the second detector 32 to follow the second X-ray source 31 by moving the second detector 32 to the position of the second X-ray source 31 in the longitudinal direction of the table 1 based on the position of the second X-ray source 31 in the longitudinal direction of the table 1 regardless of the position of the second X-ray source 31 in the short-side direction of the table 1 when the imaging information using the second imager 3 is selected and the second X-ray source 31 is manually moved. Accordingly, the second detector 32 moves in the longitudinal direction of the table 1 as the second X-ray source 31 is moved in the longitudinal direction of the table 1, and thus it is not necessary for the user to move the second detector 32 in the longitudinal direction of the table 1. Consequently, the work burden on the user due to manual movement of the second detector 32 can be reduced.

According to this embodiment, the controller 5 is configured or programmed to control the second detector 32 to follow the second X-ray source 31 by moving the second detector 32 to the first relative position based on the position of the second X-ray source 31 in the longitudinal direction of the table 1 and the irradiation angle of the second X-ray source 31 with respect to the second detector 32. Accordingly, a predetermined first relative position can be acquired based on the position of the second X-ray source 31 in the longitudinal direction of the table 1 and the irradiation angle of the second X-ray source 31 with respect to the second detector 32. Consequently, the controller 5 can move the second detector 32 to the first relative position based on the acquired information about the first relative position.

According to this embodiment, the imaging information includes a plurality of imaging modes that specify imaging methods, and the controller 5 is configured or programmed to control the second detector 32 to follow the second X-ray source 31 by moving the second detector 32 to the first relative position or moving the second detector 32 to the second relative position according to the selected imaging mode. Accordingly, the controller 5 can move the second detector 32 in the longitudinal direction of the table 1 to the first relative position or the second relative position desired by the user. Consequently, it is not necessary for the user to adjust the position of the second detector 32 in the longitudinal direction of the table 1 according to the imaging mode, and thus the imaging mode can be quickly switched.

According to this embodiment, the controller 5 is configured or programmed to control the second detector 32 to follow the second X-ray source 31 by moving the second detector 32 to the first relative position at which the central axis 62 of the second X-ray source 31 and the longitudinal center of the second detector 32 coincide with each other when the second detector 32 is caused to follow the second X-ray source 31. Accordingly, for example, in the case of an imaging mode in which the second X-ray source 31 is moved to capture a plurality of images of the same place from different angles, and a clear image is reconstructed from the plurality of captured X-ray images, the center of the irradiation range of the second X-ray source 31 is aligned with the region 91 to be imaged such that the longitudinal center of the second detector 32 can coincide with the center of an imaging range.

According to this embodiment, the controller 5 is configured or programmed to control the second detector 32 to follow the second X-ray source 31 by moving the second detector 32 to the second relative position at which the irradiation range of the second X-ray source 31 coincides with the longitudinal side of the second detector 32. Accordingly, the second detector 32 can be aligned based on the irradiation range of the X-rays emitted from the second X-ray source 31, and thus the X-rays that are not detected despite the fact that the X-rays have been transmitted through the subject 50 can be reduced. Consequently, exposure of the subject 50 to extra X-rays not related to acquisition of an X-ray image can be significantly reduced or prevented.

According to this embodiment, the second detector 32 is housed under the table 1 or pulled out from under the table 1 by manually moving the second detector 32 in the short-side direction of the table 1, and the controller 5 is configured or programmed to perform control of moving the position of the second detector 32 when the second detector 32 is housed under the table 1. Accordingly, when the second detector 32 is pulled out and only a portion of the subject 50 is imaged, the second detector 32 can be used as a table on which the region 91 to be imaged is placed. In addition, the second detector 32 moves in a state in which the second detector 32 is housed, and thus collision of the second detector 32 with the subject 50 near the table 1 can be significantly reduced or prevented.

MODIFIED EXAMPLES

The embodiment disclosed this time must be considered as illustrative in all points and not restrictive. The scope of the present invention is not shown by the above description of the embodiment but by the scope of claims for patent, and all modifications (modified examples) within the meaning and scope equivalent to the scope of claims for patent are further included.

For example, while X-rays are shown as examples of radiation in the aforementioned embodiment, the present invention is not limited to this. According to the present invention, the radiation may alternatively be commonly used radiation such as gamma rays.

While the controller of the radioscopic apparatus performs control of retracting the second detector and controls the second detector to follow the second X-ray source in the aforementioned embodiment, the present invention is not limited to this. According to the present invention, the controller of the radioscopic apparatus may alternatively either perform control of retracting the second detector or control the second detector to follow the second X-ray source.

While the first detector is an image intensifier in the aforementioned embodiment, the present invention is not limited to this. According to the present invention, the first detector may alternatively be an FPD.

While the second detector is an FPD in the aforementioned embodiment, the present invention is not limited to this. According to the present invention, the second detector may alternatively be another detector such as an image intensifier.

While the storage and the controller are provided separately from each other in the aforementioned embodiment, the present invention is not limited to this. According to the present invention, a personal computer in which a storage and a controller are integral and unitary with each other may alternatively be used, for example.

While the APR stores the imager to be used for imaging and the arrangement of the first imager or the second imager at the time of imaging in the aforementioned embodiment, the present invention is not limited to this. According to the present invention, as information different from the APR, the storage may alternatively store the information about the imager to be used for imaging and the information about the arrangement of the first imager or the second imager at the time of imaging.

While the controller performs control of retracting the second detector based on the imaging information about the region to be imaged or the retracted position in the aforementioned embodiment, the present invention is not limited to this. For example, the controller may alternatively acquire the retracted position based on the position of the first detector at the time of imaging and perform control of retracting the second detector.

While the controller controls the second detector to move to the first relative position or the second relative position according to the imaging mode in the aforementioned embodiment, the present invention is not limited to this. Information about whether the second detector is caused to follow the second X-ray source at the first relative position or the second relative position may alternatively be stored in the APR (imaging information), and the controller may alternatively perform control based on the stored imaging information.

While when the second detector contacts the switch provided in the tray, the controller performs control of retracting the second detector and controls the second detector to follow the second X-ray source in the aforementioned embodiment, the present invention is not limited to this. For example, when a sensor detects that the second detector has been housed in the tray, the controller may alternatively perform control of retracting the second detector and control the second detector to follow the second X-ray source.

What is claimed is:

1. A radioscopic apparatus configured to irradiate a subject with radiation and acquire a radiation image, the radioscopic apparatus comprising:
    a table having a placement surface on which the subject is placed;
    a first imager including a first radiation source disposed on a side of the table opposite to the placement surface, and a first detector disposed at a position that faces the first radiation source with the table interposed therebetween;
    a second imager including a second detector disposed on the side of the table opposite to the placement surface and closer to the table than the first radiation source, and a second radiation source disposed opposite to the second detector with the table interposed therebetween;
    a storage configured to store imaging information including information about an imager to be used for imaging and information about a region to be imaged of the subject; and
    a controller configured or programmed to, when the imaging information using the first radiation source is selected, perform control of retracting the second detector to a position in one of longitudinal ends of the table, at which the second detector does not block the radiation emitted from the first radiation source, according to the information about the region to be imaged of the subject included in the selected imaging information.

2. The radioscopic apparatus according to claim 1, wherein:
    the imaging information further includes information about a retracted position for the second detector based on the region to be imaged; and
    the controller is configured or programmed to perform control of retracting the second detector according to the information about the retracted position for the second detector when the imaging information using the first radiation source is selected.

3. The radioscopic apparatus according to claim 1, wherein:
    the controller is configured or programmed to control the second detector to follow movement of the second radiation source and follow the second radiation source in a longitudinal direction of the table regardless of a position of the second radiation source in a short-side direction of the table.

4. The radioscopic apparatus according to claim 3, wherein:
    the controller is configured or programmed to control the second detector to follow the second radiation source by moving the second detector to a position of the second radiation source in the longitudinal direction of the table based on the position of the second radiation source in the longitudinal direction of the table when the imaging information using the second imager is selected and the second radiation source is manually moved.

5. The radioscopic apparatus according to claim 4, wherein:
    the controller is configured or programmed to control the second detector to follow the second radiation source by moving the second detector to a first relative position based on the position of the second radiation source in the longitudinal direction of the table and an irradiation angle of the second radiation source with respect to the second detector.

6. The radioscopic apparatus according to claim 5, wherein:
    the imaging information includes a plurality of imaging modes that specify imaging methods; and
    the controller is configured or programmed to control the second detector to follow the second radiation source by moving the second detector to the first relative position or moving the second detector to a second relative position according to a selected imaging mode.

7. The radioscopic apparatus according to claim 6, wherein:
    the controller is configured or programmed to control the second detector to follow the second radiation source by moving the second detector to the first relative position at which a central axis of the second radiation source and a longitudinal center of the second detector coincide with each other when the second detector is caused to follow the second radiation source.

8. The radioscopic apparatus according to claim 6, wherein:
    the controller is configured or programmed to control the second detector to follow the second radiation source by moving the second detector to the second relative position at which an irradiation range of the second radiation source coincides with a longitudinal side of the second detector.

9. The radioscopic apparatus according to claim 1, wherein:

the second detector is housed under the table or pulled out from under the table by manually moving the second detector in a short-side direction of the table; and the controller is configured or programmed to perform control of moving a position of the second detector when the second detector is housed under the table.

* * * * *